(12) United States Patent
Stanley

(10) Patent No.: US 7,279,311 B2
(45) Date of Patent: Oct. 9, 2007

(54) USE OF NUCLEIC ACIDS BOUND TO CARRIER MACROMOLECULES

(75) Inventor: Christopher J. Stanley, Woodhurst (GB)

(73) Assignee: Oakville Trading Hong Kong Limited, Central (HK)

(*) Notice: Subject to any disclaimer, the term of this patent is extended or adjusted under 35 U.S.C. 154(b) by 0 days.

(21) Appl. No.: 09/760,819

(22) Filed: Jan. 17, 2001

(65) Prior Publication Data

US 2001/0004527 A1   Jun. 21, 2001

Related U.S. Application Data

(63) Continuation of application No. 09/313,385, filed on May 18, 1999, now Pat. No. 6,207,385.

(51) Int. Cl.
   C12P 19/34       (2006.01)
   C12Q 1/68        (2006.01)
   C07H 21/02       (2006.01)
   C07H 21/04       (2006.01)
   C07H 21/00       (2006.01)

(52) U.S. Cl. .............. 435/91.2; 435/6; 435/91.1; 536/23.1; 536/24.3; 536/24.33; 536/25.3; 536/25.32

(58) Field of Classification Search ............ 935/6, 935/7.2, 91.1, 91.2, 91.51, 183; 436/94; 536/23.1, 24.3, 24.33, 25.3, 25.32
See application file for complete search history.

(56) References Cited

U.S. PATENT DOCUMENTS

| | | | |
|---|---|---|---|
| 4,760,017 A * | 7/1988 | McCormick .............. | 435/6 |
| 4,775,619 A * | 10/1988 | Urdea ..................... | 435/6 |
| 4,876,335 A * | 10/1989 | Yamane et al. .......... | 536/27 |
| 4,988,617 A * | 1/1991 | Landegren et al. | |
| 5,220,005 A * | 6/1993 | Bronstein ............... | 536/26.21 |
| 5,308,750 A * | 5/1994 | Mehta et al. ............ | 435/5 |
| H1398 H * | 1/1995 | Campbell ................ | 435/6 |
| 5,434,257 A * | 7/1995 | Matteucci et al. ....... | 536/24.3 |
| 5,455,166 A * | 10/1995 | Walker ................... | 435/91.2 |
| 5,538,871 A * | 7/1996 | Nuovo et al. ............ | 435/91.2 |
| 5,648,213 A * | 7/1997 | Reddy et al. ............ | 435/6 |
| 5,652,099 A * | 7/1997 | Conrad .................. | 435/6 |
| 5,667,976 A * | 9/1997 | Van Ness et al. ........ | 435/6 |
| 5,700,921 A * | 12/1997 | Westling et al. ......... | 536/22.1 |
| 5,753,437 A * | 5/1998 | Steeg et al. .............. | 435/6 |
| 5,792,608 A | 8/1998 | Swaminathan et al. | |
| 5,814,445 A * | 9/1998 | Belyavsky et al. ....... | 435/6 |
| 5,856,092 A * | 1/1999 | Dale et al. ............... | 435/6 |
| 5,908,972 A * | 6/1999 | Houtz ..................... | 800/205 |
| 6,004,747 A | 12/1999 | Olsen et al. | |
| 6,004,783 A * | 12/1999 | Ausubel et al. .......... | 435/91.2 |
| 6,011,020 A * | 1/2000 | Gold et al. ............... | 514/44 |
| 6,027,889 A * | 2/2000 | Barany et al. ........... | 435/6 |
| 6,207,385 B1 * | 3/2001 | Stanley .................. | 435/6 |

FOREIGN PATENT DOCUMENTS

| | | |
|---|---|---|
| DE | 43 01 693 | 7/1994 |
| DE | 195 18 217 | 11/1995 |
| WO | 88/01302 | 2/1988 |
| WO | 90/06042 | 6/1990 |
| WO | 90/11369 | 10/1990 |
| WO | 91/00868 | 1/1991 |
| WO | 93/01498 | 1/1993 |
| WO | 96/04898 | 1/1993 |
| WO | 94/02634 | 2/1994 |
| WO | 96/04404 | 2/1996 |
| WO | 96/13609 | 5/1996 |
| WO | 96/31622 | 10/1996 |
| WO | 98/22620 | 5/1998 |

OTHER PUBLICATIONS

Lee et al., A method for obtaining high-quality sequences from the non-biotinylated, free ssDNA remaining after solid-phase sequencing. BioTechniques, 14, 191 and 192, 1993.*
Mercier et al., Direct PCR from whole blood, without DNA extraction. Nucleic Acids Res., 18, 5908, 1990.*
Maniatis et al., Molecular Cloning: A Laboratory Manual (1982), pp. 164 and 165. Published by Cold Spring Harbor Laboratory, Box 100, Cold Spring Harbor, New York.*
The Merck Index (8 th Edition), p. 501, published by Merck & CO., Inc., Rahway, NJ , USA.*
Debre, P. et al., An in situ PCR method for detecting and quantifying a nucleic acid in a population of animal cells, CAPLUS, 2002.*
Stephens et al., Transcriptional repression of the GLUT4 and C/EBP genes in 3T3-L1 adipocytes by tumor necrosis factor-alpha. J. Biol. Chem., 266, 21839-21845, 1991.*
McCormick et al., Alkaline phosphatase labeling of oligos: choosing the best LIGHTSMITH™ system for your non-isotopic labeling and detection needs. Promega Notes magazine No. 40, 1993, p. 04.*
Attachment for fluorescein.*
Attachment for dextran.*
Attachment for lysine and polylysine.*
Attachment for alkaline phosphatase.*

* cited by examiner

*Primary Examiner*—Frank Lu
(74) *Attorney, Agent, or Firm*—Morrison & Foerster LLP

(57) ABSTRACT

A nucleic acid primer is bound to a soluble carrier macromolecule, a multitude of primer molecules thus being carried by each carrier macromolecule, and hybridisation of the primer to a template followed by extension of the primer to replicate the template in complementary form is carried out as part of a PCR procedure or other amplification, or to form an extended primer of greater hybridisation affinity. A second primer used in the amplification may also be bound to a carrier macromolecule.

30 Claims, 1 Drawing Sheet

LANES: 1 2   4 5   7 8 9 10   12 13

LANE 1, 2, 7, 8, 9 - PCR PRODUCT ON DEXTRAN PRIMER
LANE 4, 13 - DNA STANDARDS
LANE 5 - DEXTRAN PRIMER BEFORE PCR
LANE 12 - POSITIVE CONTROL (LISTERIA DNA + LM23, 24 PRIMER)

LANES:   3  4 5 6 7 8 9

LANE 3, 7 - PCR PRODUCT ON DEXTRAN PRIMER (NO ADDED MAGNESIUM CHLORIDE)
LANE 4, 8 - PCR PRODUCT ON DEXTRAN PRIMER (1µl ADDED MAGNESIUM CHLORIDE)
LANE 5, 9 - PCR PRODUCT ON DEXTRAN PRIMER (2µl ADDED MAGNESIUM CHLORIDE)
LANE 6 - NEGATIVE CONTROL

USE OF NUCLEIC ACIDS BOUND TO CARRIER MACROMOLECULES

This is a continuation division of application Ser. No. 09/313,385, filed 18 May 1999, now U.S. Pat. No. 6,207,385.

The present invention relates to processes involving the use of nucleic acids such as oligonucleotides bound to carrier macromolecules and to new forms of immobilised nucleic acids.

Many different processes have been devised involving the use of nucleic acids such as oligonucleotides. These include assay procedures such as hybridisation assays in which the ability of a probe oligonucleotide of a given base sequence to recognise and bind a nucleic acid of complementary sequence is utilised. They include also amplification procedures in which a nucleic acid template of a given sequence is replicated. Such amplification procedures involve the use of primers which are complementary in sequence to a portion of the sequence to be replicated.

The product of such an amplification procedure is generally a nucleic acid in solution in the reaction mixture. Work up procedures are generally then needed to isolate or to detect the amplification product. Attempts have been made to adapt such amplification procedures to operate with the or a primer oligonucleotide immobilised to a solid support, e.g. a magnetic bead, to make it easier to collect the amplification product. However, such steps have usually interfered with the amplification to some extent.

WO96/31622 discloses the binding of oligonucleotides directly to a solid support, e.g. aminated polypropylene. The tethered oligonucleotides are used as primers for DNA-dependent synthesis by DNA polymerase.

WO96/13609 discloses a solid phase nucleic acid amplification using an oligonucleotide primer immobilised on a functionalised solid support. The primer is linked to the support by a polyfunctional molecule. The linker molecules are of relatively low molecular weight, e.g. analogs of decamer oligonucleotides.

WO96/04404 discloses carbonylated latex bead having oligonucleotide primers directly bonded thereto for use in hybridisation and amplification reactions.

Alternatively, oligonucleotides may be bonded to the surface of an epoxysilane derivativized solid support via respective relatively low molecular weight linker molecules, e.g. hexamethylene glycol.

WO91/00868 discloses oligonucleotides linked to a solid support via a dithio (—S—S—) bridge. Part of the oligonucleotide acts as a spacer between a sequence having relevant specificity and the susbtrate. Target oligonucleotides are hybridised to the immobilised specific sequence, which is then extended to incorporate labelled nucleotides.

WO90/0604 discloses attaching DNA probes to magnetic particles. The magnetic particles are used in an assay in which the attached probe sequences are hybridised and extended to incorporate a label. The magnetic beads are coupled to streptavidin and the probe sequences are biotinylated for attachment to the streptavidin coupled beads.

WO93/01498 describes methods for conjugating a carrier macromolecule to any of various molecular species, including oligonucleotides and polynucleotides, via a divinylsulphone based chemistry. The carrier macromolecule is typically a polysaccharide such as dextran. The carrier macromolecule may also be conjugated to a second molecular species which acts as a label.

Figure 1A:
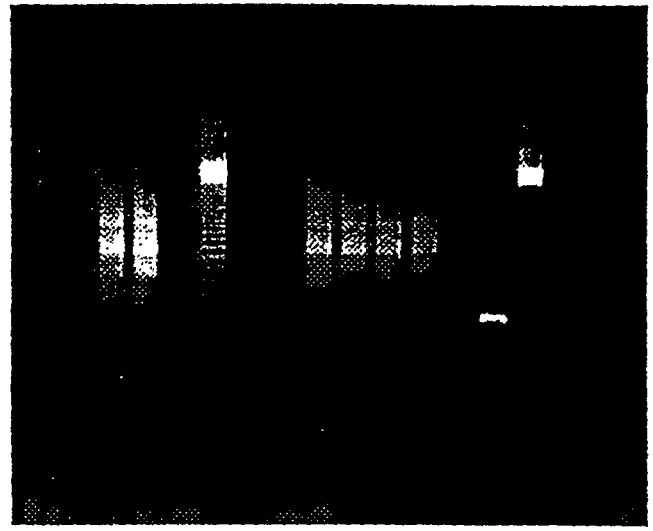
FIG. 1a—PCR reactions using DNA purified from *Listeria monocytogenes* and DNA primers specific for sequences of *Listeria monocytogenes* designated LM23 (23 base pairs) and LM24 (24 base pairs) that are linked to a dextran polymer of high molecular weight.

We have now devised various processes in which such nucleic acids bound to carrier macromolecules may be used advantageously. In a first aspect of the invention, it has surprisingly been found that amplification processes proceed well using primer which is bound to a carrier macromolecule.

Accordingly, in a first aspect, the invention provides a process for the replication of a nucleic acid template comprising hybridising to said template a primer having a sequence complementary to a portion of said template, which primer is bound to a carrier macromolecule, and extending said primer to replicate said template in complementary form.

Preferably, the carrier macro molecule is a natural or synthetic polysaccharide, a homopolyamino acid, a natural or synthetic polypeptide or protein, or a synthetic polymer having nucleophilic functional groups, for instance a polyvinyl alcohol, a polyallyl alcohol or polyethylene glycol or a substituted polyacrylate.

More preferably however, the carrier macromolecule is a dextran, which term includes carboxymethyl-dextrans, a starch, an hydroxyethyl-starch, an hydroxypropyl-starch, a glycogen, an agarose derivative or cellulose derivative, including hydroxyethyl- and hydroxypropyl-celluloses, or a natural gum.

Preferably, the carrier macro molecule in its free state is substantially linear and substantially uncharged at a pH in the range of about 4 to about 10. Preferably, it is water soluble and it suitably has a peak molecular weight in the range of about 1,000 to about 40,000,000, e.g. over 10,000 or over 100,000 or over 1,000,000.

Typically, a multitude of primer molecules will be bound to each carrier macromolecule.

As described in WO93/01498, using one possible conjugation chemistry the primer is bound to said carrier macro molecule via one or more moieties derived from divinyl sulphone, each of which moieties is attached to each of the carrier macromolecule and the primer by a covalent linkage formed between one of the two vinyl groups of a divinyl sulphone molecule and a reactive functionality on the carrier macromolecule or primer.

In the replication or amplification process, the primer may be extended by the action of a polymerase incorporating nucleotides on to said primer, e.g. in a polymerase chain reaction (pcr), strand displacement amplification (sda), self-sustained sequence replication (3sr) or nucleic acid sequence-based amplification (nasba) amplification procedure. Such procedures as previously practised are all well described in the literature.

Accordingly, according to a preferred practice of the invention, said template is a double stranded template and is denatured to single stranded form, said carrier macromolecule-bound primer is complementary in sequence to a region of a first one of the template strands and a second primer is provided which is complementary in sequence to a region of the other strand, which second primer is also extended so as to form a complementary sequence copy of said template second strand.

Alternatively, the primer may be extended by the action of a ligase ligating said primer to at least one further primer hybridised to said template, e.g. in an LCR (ligase chain reaction).

Where more than one primer is required in the replication or amplification procedure, one or more of said primers may be of the kind characterising this invention and the remainder may be conventional or otherwise modified oligonucleotides. Accordingly, the invention includes processes in which a second primer is extended or ligated in said amplification procedure which is also bound to a carrier macromolecule.

Optionally, during the extension of a said primer, a detectable marker is incorporated into the extended primer.

In a particularly advantageous aspect of the invention, the carrier macro molecule is itself bound to a solid support. Amplification products produced in the replication process will therefore themselves become bound to the support and can be removed from the reaction mixture for further treatment simply by removal of the support. The solid support may take many forms such as plates, strips, containers (including microtitre plate wells or eppendorf tubes), beads, membranes, or magnetic beads. This differs significantly from prior art schemes in which individual oligonucleotide molecules are linked to a solid support by respective low molecular weight linker molecules.

The extension of the primer may be conducted in situ in a biological sample. Thus the process may be one in which said biological sample is a plant or animal tissue sample, microorganism culture, or microorganism culture medium and the process may be in situ PCR where the much lower diffusion of the PCR product on the carrier macromolecule is advantageous in localising the amplified DNA in situ.

The product of the replication methods described above will normally be a nucleic acid bound to the carrier macromolecule formed by extension or ligation of a primer nucleic acid. In accordance with a second aspect of the invention there is provided a method of detecting the presence of such a nucleic acid bound to a carrier macromolecule, whether produced by the processes described above or by some different process. The detection method according to the second aspect of the invention comprises providing a second nucleic acid bound to a carrier macromolecule, contacting said nucleic acids under hybridisation conditions and detecting hybridisation between said nucleic acids.

Because both of the nucleic acids involved are bound to carrier macromolecules, the hybridisation will produce aggregation of the macromolecules which will be detectable in a number of ways. These may according to circumstances include changes in the light scattering properties of the reaction mixture or the formation of a gel or changes in fluorescent, luminescent, or electrochemical properties.

In conducting hybridisation dependent procedures such as hybridisation assays or amplification procedures, it is often desirable to have available a relatively long probe or primer of a sequence complementary to the sequence to be detected in an assay or to bind specifically to the primer in an amplification. Generally, the efficiency of these procedures will be greater with longer primers or probes because of their higher affinity. However, the synthesis of long oligonucleotides is burdensome. In a third aspect, the present invention provides a convenient method of producing longer probes or primers or other oligonucleotides without the need for extensive synthesis, making use of the features of the invention already described.

In accordance with this aspect of the invention, there is provided a process for producing an extended oligonucleotide, e.g. for use as a probe or replication primer, by the replication of a nucleic acid template comprising hybridising to said template a starting primer having a sequence complementary to a portion of said template, which starting primer is bound to a carrier macromolecule, and extending said starting primer to replicate at least a portion of said template in complementary form so as to generate said extended oligonucleotide.

Such an extended oligonucleotide may then be used in amplification or assay procedures as described above. In particular, this aspect of the invention includes a method of detecting a nucleic acid sequence comprising making a probe for detecting said sequence by using said sequence as a template sequence in a method as just described such that said probe comprises said extended double-stranded oligonucleotide having a sequence complementary to said sequence to be detected bound to said carrier macromolecule, removing one of the strands of oligonucleotide by denaturation and separation of the products, and using the probe to detect the nucleic acid sequence in a sample by hybridisation thereto.

This aspect of the invention also includes a method of replication of a nucleic acid sequence comprising making an extended primer or hybridisation probe by using said sequence as a template sequence in a method of primer extension as just described such that said extended primer comprises said extended oligonucleotide having a sequence complementary to said sequence to be detected bound to said carrier macromolecule, removing any free nucleic acid not bound to said carrier macromolecule therefrom, and using the extended primer in a nucleic acid replication procedure such as pcr or any of the other amplification procedures referred to above.

The invention includes also a nucleic acid bound to a carrier macromolecule, which macromolecule is itself bound to a solid support and the use of such an immobilised nucleic acid as a primer or probe.

As indicated above, nucleic acids may be bound to carrier macromolecules as described in WO93/01498, although other techniques may be used.

Owing to the nature of the coupling chemistry employed following the teaching of WO93/01498 for preparing conjugates, i.e. the establishment, on the polymeric carrier molecule, of covalently bound reactive moieties deriving from divinyl sulfone, and the establishment of covalent bonds between, on the one hand, such moieties, and, on the other hand, nucleotide sequences, the known pattern of reactivity of the vinyl groups in a species such as divinyl sulfone will generally require that the reactive functionality on the polymeric carrier, i.e. the group with which a vinyl group of divinyl sulfone will react to form a covalent bond, is a nucleophilic function. Suitable polymeric carriers will then be, for example, polymeric carriers with functional groups such as: —O$^-$ (e.g. deprotonated phenolic hydroxy groups, such as deprotonated aromatic hydroxy groups in tyrosine residues of polypeptides or proteins), —S$^-$ (e.g. deprotonated thiol groups on aromatic rings or aliphatic groups, such as deprotonated thiol groups in cysteine residues of polypeptides or proteins), —OH (e.g. aliphatic hydroxy groups on sugar rings, such as glucose or other monosaccharide rings in oligo- or polysaccharides; or alcoholic hydroxy groups in polyols, such as polyethylene glycols; or alcoholic hydroxy groups in polyols, such as polyethylene glycols; or hydroxy groups in certain amino acid residues of polypeptides or proteins, such as serine or threonine residues), —SH (e.g. thiol groups in cysteine residues of polypeptides or proteins), primary amino groups (e.g. in lysine or ornithine residues of polypeptides or proteins; or in amino-substituted sugar rings in certain polysaccharides or derivatives thereof, such as chitosan) or secondary amino groups (e.g. in histidine residues of polypeptides or proteins). For similar reasons, the functional group in question the nucleotide sequence will also normally be a nucleophilic function.

The water-soluble polymers which function as the carrier molecules in reagents and conjugates may be chosen from a wide variety of types of polymers, including:

natural and synthetic polysaccharides, as well as derivatives thereof, for example dextrans and dextran derivatives, starches and starch derivatives, cellulose derivatives, amylose and pectin, as well as certain natural gums and derivatives thereof, such as gum arabic and salts of alginic acid;

homopoly (amino acid)s having suitable reactive functionalities, such as polylysines, polyhistidines or polyornithines;

natural and synthetic polypeptides and proteins, such as bovine albumin and other mammalian albumins; and synthetic polymers having nucleophilic functional groups, such as polyvinyl alcohols, polyallyl alcohol, polyethylene glycols and substituted polyacrylates.

Very suitable polymers for the purpose of the invention are polysaccharides and derivatives thereof, for example: dextrans, carboxymethyl-dextrans, hydroxyethyl- and hydroxypropyl-starches, glycogen, agarose derivatives, and hydroxyethyl- and hydroxypropyl-celluloses. As will be apparent from the working examples herein (vide infra), notably dextrans have proved to be particularly suitable polymers in connection with the invention, and they are presently the most preferred polymers.

Depending on the use to which a reagent or conjugate of the invention is to be put, reagents and conjugates of the invention may be based on water-soluble polymeric carriers having molecular weights ranging from rather low to very high, and in a further aspect of the invention the polymeric carrier may have a peak molecular weight in the range of about 1,000 to about 40,000,000. Peak molecular weights which are of considerable interest, and which are exemplified in the working examples given herein, are peak molecular weights in the range of about 1,000 to about 80,000, and in the range of about 80,000 to about 2,000,000. A peak molecular weight of particular interest, notably in the case of dextrans as polymeric carriers, is a peak molecular weight of about 500,000.

The term "peak molecular weight" (also denoted "peak average molecular weight") as employed in the present specification and claims in connection with polymeric carriers denotes the molecular weight of greatest abundance, i.e. that molecular weight (among a distribution of molecular weights) which is possessed by the greatest number of molecules in a given sample or batch of the polymer. It is quite normal to characterise numerous types of polymers in this manner, owing to the difficulty (particularly for the highest molecular weights) of obtaining or preparing polymer fractions of very narrow molecular weight distribution. In the case of numerous commercially available polymers which are of interest in the context of the invention, for example dextrans, the manufacturer or distributor will be able to provide reliable peak molecular weight data (determined for examples, by gel-permeation chromatography) which can provide a basis for the selection of a polymer fraction suitable for the preparation of a particular type of reagent or conjugate. It should be mentioned here that peak molecular weight values cited in the present specification and claims refer to the peak molecular weight of the free polymer in question, and take no account of, for example, the possible formation of cross-linked polymer units, e.g. as a result of cross-linking of two or more polymer molecules by reaction with divinyl sulfone; such cross-linked units will, on average, have higher molecular weights than the individual free polymer molecules from which they are formed.

Reagents for use in the present invention may clearly be tailored to meet a very wide range of requirements with regard to peak molecular weight of the polymer and the content of free, reactive vinyl groups. A further aspect of the invention relates to reagents based on a polymeric carrier having a peak molecular weight of about 500,000 or about 2,000,000, or having a peak molecular weight in any one of the following ranges:

about 1,000 to about 20,000; about 20,000 to about 80,000; about 80,000 to about 500,000; about 500,000 to about 5,00,000; or about 5,000,000 to about 40,000,000;

and having a content of free, reactive vinyl groups in the range of about 1 to about 5,000 µmoles of vinyl groups per gram of polymeric carrier, such as in any of the following sub-ranges (expressed in µmoles of vinyl groups per gram of polymeric carrier):

about 1 to about 50; about 50 to about 300; about 300 to about 1,000; or about 1,000 to about 5,000.

Molecular species which in addition to nucleotide sequences may be attached to the polymeric carrier of a conjugate used in the invention, are to be found among numerous types of substances, examples being:

amino acids; oligopeptides, such as $(His)_6$ sequences; proteins, such as ferritin, phycoerythrins, phycocyanins or phycobilins; enzymes, such as horseradish peroxidase, alkaline phosphatase, glucose oxidase, galactosidases or ureases; toxins; drugs; dyes; fluorescent, luminescent, phosphorescent or other light-emitting substances; metal-chelating substances, such as iminodiacetic acid, ethylenediaminetetraacetic acid (ETDA), diethylenetriaminepentaacetic acid (DTPA) or desferrioxamine B; substances labelled with a radioactive isotope; or substances labelled with a heavy atom.

In the light of the discussion given earlier, above, it will be clear that the majority of types of substances among these latter examples will be able to serve as labels or markers in conjugates according to the invention. To give some further examples, fluorescent substances may be selected from, e.g. fluorescein (suitably as fluorescein isothiocyanate, FITC), fluoresceinamine, 1-naphthol, 2-naphthol, eosin, erythrosin, morin, o-phenylenediamine, rhodamine and 8-anilino-1-naphthalenesulfonic acid. Radioactive isotopes of relevance may be selected, for example, among isotopes of hydrogen (i.e. tritium, $^3H$), carbon (such as $^{14}C$), phosphorus (such as $^{32}P$), sulfur (such as $^{35}S$), iodine (such as $^{131}J$), bismuth (such as $^{212}Bi$), yttrium (such as $^{90}Y$), technetium (such as $^{153}Sm$). Heavy atoms of relevance may be selected for example, among Mn, Fe, Co, Ni, Cu, Zn, Ga, In, Ag, Au, Hg, I, Bi, Y, La, Ce, Eu and Gd. Gold (Au) [possibly in combination with silver (Ag) as an enhancement reagent (vide supra)] is a particularly useful heavy atom in many cases.

Suitable methods comprise allowing the water-soluble polymeric carrier to react with divinyl sulfone in aqueous solution at a pH above 5. In its most general form, the reaction may take place at a temperature in the range of 0-60° C., although a temperature in the range of 20-25° C. will often be quite suitable. The pH at which the reaction takes place is generally within the range of about 10-11.5, which is a pH range in which divinyl sulfone is particularly reactive towards reactive functionalities on most types of polymeric carriers.

As far as the concentration of the polymeric carrier in the aqueous solution is concerned, it will generally be within the range of 0.1-20% w/v, and often in the range of 1-10% w/v. The concentration of divinyl sulfone in the aqueous solution will generally be in the range of 0.1-15% v/v, and often in the range of 1-10% v/v.

It is difficult to give general guidelines concerning the period of time for which the reaction of divinyl sulfone with the polymeric carrier in aqueous solution should be allowed to proceed, since these will vary rather considerably, depending, e.g. the temperature and pH at which the reaction occurs, the concentration of the polymeric carrier and of divinyl sulfone in the reaction mixture, the nature and/or molecular weight of the polymeric carrier, and the extent to which cross-linking of the polymeric carrier (by reaction with divinyl sulfone) may proceed before there is a risk, for example, of gelling or precipitation taking place; as is clearly illustrated in the working examples herein in the case of dextrans, the reaction time may be an important factor for at least some classes of polymeric carriers. The reaction time in question will, however, normally be within the range of 5-120 minutes.

The intermediate so produced may be purified by a process such as dialysis (for the removal of unwanted salts or other species or low molecular weight) or gel chromatography.

As regards the reaction of the water-soluble intermediate reagent with the nucleotide sequence or labelling reagent, the temperature during the reaction will generally be in the range of 0-60° C., and often in the range of 20-25° C. The concentration of molecular species in the aqueous reaction medium will generally be in the range of 0.1-20% w/v, and the pH of the solution will generally be in the range of about 8-12.

Preferably, the aqueous solution in which the molecular species reacts with the optionally purified water-soluble intermediate reagent contains a lyotropic salt, i.e. a salt which has the property, e.g. of promoting the precipitation ("salting-out") of certain types of high molecular weight species, in particular proteins, from aqueous solution. The effectiveness of the incorporation of such a lyotropic salt in enhancing the attachment of molecular species such as oligonucleotides to the reactive vinyl groups present in the water-soluble intermediate reagent is contemplated to derive from the "salting-out" effect mentioned above.

Suitable lyotropic salts may be selected among sulfates, phosphates, citrates and tartrates of lithium, sodium, potassium and ammonium, and the lyotropic salt will normally be present in a concentration corresponding to an ionic strength of at least 0.01, for example a concentration corresponding to an ionic strength of at least 0.3. A suitable concentration will often be a concentration corresponding to an ionic strength in the range of 0.5-5.

As already indicated above, the influence of lyotropic salts in methods of the invention is particularly noteworthy in the case of molecular species which are proteins or polypeptides.

Any remaining free vinyl groups present in the conjugate formed may be deactivated by the addition, to the aqueous solution of the conjugate, of an excess of a deactivating species of low molecular weight; suitable deactivating species may be, for example, ethanolamine, mercaptoethanol, or certain amino acids, e.g. cysteine, glycine, alanine or valine.

Figure 1B:
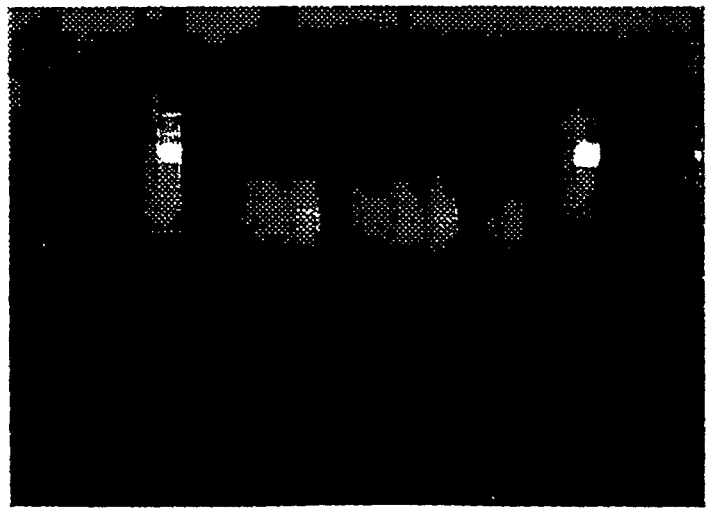
FIG. 1b—PCR reactions using DNA purified from *Listeria monocytogenes* and DNA primers specific for sequences of *Listeria monocytogenes* designated LM23 (23 base pairs) and LM24 (24 base pairs) that are linked to a dextran polymer of high molecular weight in the presence or absence of $MgCl_2$.

The invention will be illustrated and further described by the following examples in which reference is made to the accompanying drawings wherein FIGS. 1a and 1b show gels produced in Example 2.

EXAMPLE 1

Coupling of Amino-primer LM23 to 25% Activated Dextran MW 500,000 Followed by a Gelfiltration in Low Concentration of Salt.

Dextran (peak Mw=500,000) (Pharmacia Biotech, Uppsala, Sweden) was activated with divinyl sulphone (activation level 25 percent of hydroxyl groups) according to the methods given in WO93/01498 (Example 4—solution B). An oligonucleotide primer consisting of 23 nucleotide bases having a sequence from *Listeria monocytoaenes* having at its 5' end a primary amine group introduced through an amino modified nucleotide base supplied by DNA Technology, Aarhus, Denmark, was coupled to the activated Dextran at 30° C. overnight, in 1.75M phosphate, pH of 10.4 at a molar ratio of 100 oligonucleotide primer:1 activated dextran.

After coupling the Dex-Primer product was gelfiltered on Superdex 200 in 10 mM NaCl to remove excess uncoupled amino primer.

It was found that 32 molecules of primer on average were coupled to each molecule of dextran using absorbance measurements at A260 nm.

EXAMPLE 2

PCR using a Dextran Coupled Primer.

Primers for *Listeria monocytogenes* LM23 (23 base pairs) and LM24 (24 base pairs), were supplied by DNA Technology, Aarhus, Denmark.

A PCR reaction was set up in an Eppendorf tube as follows: 10 µl LM 23 dex primer, 5 µl LM 24 primer (not coupled to dextran), 5 µl purified *Listeria monocytogenes* DNA, 0 µl, 1 µl or 2.5 µl of 25 mM $MgCl_2$ stock, 25 µl PCR Master Mix from Boehringer Mannheim (Mannheim, Germany) (which contains all the dNTPs and the Taq polymerase), 50 µl distilled water. There were 29 cycles of 94° C., 30 seconds; 55° C., 30 seconds; 72° C., 1 minute in a Perkin Elmer 9600 instrument. The PCR products were separated using a standard gel electrophoresis procedure on a 2% agarose gel and stained with Cyber Green (from Molecular Probes Inc., California) for visualisation. The resulting gel, shown in FIG. 1a, shows in Lane 5 the dextran primer, before PCR, indicating that the Cyber Green dye binds to the short oligonucleotide primers attached to the dextran. The dextran primer is of high molecular weight and polydisperse. In Lane 12 the control PCR product using "normal" LM23 and LM24 primers is seen, this has a size of 350 bp. The PCR product synthesised with the dextran LM23 primer in 1 mM $MgCl_2$ is shown in Lane 1, 2, 7, 8, 9, 10. This is of high molecular weight and polydisperse, with a minor contaminant of 350 bp originating from the free LM 23 primer contaminating the dextran primer. In FIG. 1b Lanes 3 and 7 shows the product made with no added $MgCl_2$ in the PCR mix. Lanes 4 and 8 shows the product made with 1 µl of 25 mM MgCL$_2$ stock added to the PCR mix. Lanes 5 and 9 show the product with 2 µl MgCl$_2$ added. There is more high molecular weight PCR product produced in the higher magnesium concentration, as indicated by the greater staining intensity in the gel.

EXAMPLE 3

Incorporation of Biotin in PCR Products Made with a Dextran Primer.

Example 2 was repeated except that 0.8 µl of a 100 µM solution in water of biotin dUTP supplied by Sigma, Copenhagen, Denmark, was added to the Boehringer Master mix before PCR. The biotinylated PCR products were separated on an agarose gel as described in Example 2. A Southern blot using a Hybond N nylon membrane (Amersham International, Cardiff, UK) was prepared from the gel using standard techniques. The membrane was illuminated with UV light for 2 minutes to crosslink the DNA, washed briefly with distilled water and then incubated for two hours with streptavidin-horse radish peroxidase conjugate (AMDEX A/S, Copenhagen, Denmark) diluted 1:100 in 0.1M potassium phosphate pH 7.2, 0.5% Tween 20, 5% bovine serum albumin. The membrane was washed three times in this buffer and then immersed in a solution of DAB peroxidase substrate (Kem-en-Tec A/S, Copenhagen, Denmark). The brown product from the DAB substrate was deposited on the nylon membrane indicating the presence of the biotinylated DNA products. The agarose gel was also stained with Cyber green and the Southern blot and stained gel were compared. The pattern was identical to the gel depicted in Example 2, except that in the Southern blot the primers did not stain since they did not incorporate biotin during the PCR process. This experiment confirms that de novo synthesis of DNA takes place on the primers to incorporate the biotinylated dUTP.

EXAMPLE 4

Coupling the Dextran Primer to a Microplate Well and use as a Capture Probe for PCR Products.

Nucleolink (Nunc A/S, Denmark) microwell strips were used, these have an amino group on the surface of the plastic. The dextran primer prepared in Example 1 was diluted ten fold in 1.75M potassium phosphate buffer pH 10.4 and added to the wells of a Nucleolink plate. The wells were incubated for 3 hours and washed with distilled water. A solution of 5 µl biotinylated PCR product, made as described in Example 3 except using normal i.e. not dextran primers, in 5 ml 2×SSC buffer containing 1% SDS was prepared and 100 µl was added to the wells. The wells were heated to 95° C. for 2 minutes to denature the double-stranded PCR product and then incubated for a further 2 hours at 55° C. The wells were then washed with 0.1M potassium phosphate buffer, pH 7.2, 0.5% NaCl, 0.1% Tween 20 and then incubated for one hour with streptavidin-horse radish peroxidase conjugate (AMDEX A/S, Copenhagen, Denmark) diluted 1:100 in 0.1M potassium phosphate pH 7.2, 0.5% Tween 20, 5% bovine serum albumin (100 µl per well). The wells were then washed three times with the phosphate buffer and 100 µl of TMB substrate (Kem-en-Tec A/S, Copenhagen, Denmark) was added to each well. The absorbance was read at 450 nm. A mean absorbance of 1.6 (n=8) was measured for the wells where dextran primer had been bound to the surface of the well, a mean absorbance of 0.19 (n=8) was measured in a control well (no dextran primer). The Example shows that dextran primer becomes bound to the surface of the amino plastic wells and is capable of hybridising to DNA of complementary sequence.

EXAMPLE 5

PCR on a Solid Phase using Immobilised Dextran Primer.

The Nucleolink wells prepared in Example 5 were used in a PCR process. 100 µl of the Boehringer Master mix, incorporating biotin as described in Example 3 was added to the dextran primer coated wells. The PCR using *Listeria monocytogenes* DNA was carried out as described in Example 2 using a heat block on the instrument into which the Nucleolink wells were placed. After the PCR, the wells were washed with 0.1M potassium phosphate pH 7.2, 0.5% Tween 20, 5% bovine serum albumin and the streptavidin peroxidase conjugate was added to each well as described in Example 4. After washing the wells and adding TMB substrate the absorbance was measured at 450 nm. In the wells coated with dextran primer the mean absorbance was 1.9 (n=8), in the uncoated control wells the mean absorbance was 0.24 (n=8). This shows that biotinylated PCR products were synthesised on the surface of the dextran primer coated microwell during a PCR process in the well.

The invention claimed is:

1. A process for amplification of a nucleic acid template comprising:
   providing a primer covalently bound to a non-nucleotide carrier macromolecule;
   hybridizing the bound primer to said template;
   extending said bound primer to form an extended primer which replicates from said template,
   wherein said carrier macromolecule is a dextran that is water soluble at a temperature in the range of 0-60° C. and has a peak molecular weight in the range of about 1,000 to about 40,000,000 Daltons; and
   performing amplification of the nucleic acid template.

2. The process of claim 1 wherein the non-nucleotide carrier macromolecule further comprises a label.

3. The process of claim 2 wherein the label is a fluorescent label.

4. A process for amplification of a nucleic acid template comprising:
   providing a first primer bound to a non-nucleotide carrier macromolecule via one or more moieties derived from divinyl sulfone located on the non-nucleotide carrier macromolecule;
   hybridizing the bound first primer to said template;
   extending said bound first primer to form an extended primer which replicates from said template;
   wherein the non-nucleotide carrier macromolecule is a dextran; and
   performing amplification of the nucleic acid template.

5. The process as claimed in claim 4, wherein the non-nucleotide carrier macromolecule in its free state is substantially linear and substantially uncharged at a pH in the range of 4 to 10.

6. The process as claimed in claim 5, wherein said non-nucleotide carrier macromolecule has a peak molecular weight in the range of 1,000 to about 40,000,000 Daltons or 80,000 to about 500,000 Daltons.

7. The process as claimed in claim 4, wherein said non-nucleotide carrier macromolecule is water soluble and has a molecular weight in excess of 80,000 Daltons.

8. The process as claimed in claim 4, wherein said primer is bound to said non-nucleotide carrier macromolecule by a covalent linkage formed between one of the two vinyl groups of the divinyl sulphone on the non-nucleotide carrier macromolecule and a reactive group on the first primer.

9. The process as claimed in claim 4, wherein said first primer is extended by a polymerase wherein said polymerase incorporates nucleotides into said first primer.

10. The process as claimed in claim 4, wherein said primer is extended in a polymerase chain reaction (pcr), strand displacement amplification (sda), self-sustained sequence replication (ssr) or nucleic acid sequence-based amplification (nasba) amplification procedure.

11. The process as claimed in claim 7, further comprising hybridizing at least two other primers to said template wherein said first primer is extended by the action of a ligase sequentially ligating said first primer to the at least two other primers hybridised to said template.

12. The process as claimed in claim 4, wherein said template is a double stranded template and is denatured to a single stranded form, said bound first primer is complementary in sequence to a region of one of the template strands and a second primer is provided which is complementary in sequence to a region of the other strand of the template, and the second primer is also extended to form another extended primer which is complementary to said template other strand.

13. The process as claimed in claim 4, wherein said non-nucleotide carrier macromolecule is bound to a solid support.

14. The process as claimed in claim 9, further comprising using a second primer wherein said second primer is extended in said amplification and said second primer is also bound to a carrier macromolecule.

15. The process as claimed in claim 11, wherein one of said at least two other primers which is ligated by said ligase is also bound to a carrier macromolecule.

16. The process as claimed in claim 15, wherein during the extension, a detectable marker is incorporated into one of the extended primers.

17. The process as claimed in claim 12, wherein said extension of first primer or the second primer is conducted in situ in a biological sample.

18. The process as claimed in claim 17, wherein said biological sample is a plant or animal tissue sample, microorganism culture, or microorganism culture medium.

19. The process of claim 4 wherein the non-nucleotide carrier macromolecule further comprises a label.

20. The process of claim 19 wherein the label is a fluorescent label.

21. A method of detecting a nucleic acid sequence in a sample, comprising:
providing a primer bound to a non-nucleotide carrier macromolecule via one or more moieties derived from divinyl sulfone located on the non-nucleotide carrier macromolecule, wherein the non-nucleotide carrier macromolecule is a dextran;
hybridizing the bound primer to a portion of the target nucleic acid sequence;
extending the bound primer to form an extended primer which replicates from the target nucleic acid sequence to form an amplified probe that is complementary to the target nucleic acid sequence;
hybridizing the amplified probe to the target nucleic acid sequence in the sample; and
detecting a hybrid formed between the amplified probe and the target nucleic acid sequence to detect the target nucleic acid sequence in the sample.

22. A process for replication of a nucleic acid template comprising:
providing a primer being bonded to a carrier macromolecule which is a dextran;
hybridizing the bound primer to said template; and
extending said bound primer to form an extended primer which replicates from said template,
wherein said primer is bound to said carrier macromolecule via one or more moieties derived from divinyl sulphone,
at least one of the moieties is attached to the carrier macromolecule by a covalent linkage formed between one of the two vinyl groups of the divinyl sulphone molecule of the at least one of the moieties and a reactive group on the carrier macromolecule, and
at least one of the moieties is attached to the primer by a covalent linkage formed between one of the two vinyl groups of the divinyl sulphone molecule of the at least one of the moieties and a reactive group on the primer.

23. The process of claim 22, wherein said dextran in its free state is substantially linear and substantially uncharged at a pH in the range of 4 to 10.

24. The process of claim 22, wherein said dextran has a peak molecular weight in the range of 1,000 to 40,000,000.

25. The process of claim 22, wherein said primer is extended in a polymerase chain reaction (pcr), strand displacement amplification (sda), self-sustained sequence replication (3sr) or nucleic acid sequence-based amplification (nasba) amplification procedure.

26. The process of claim 22, wherein said primer is extended by the action of a ligase ligating said primer to at least one further primer hybridized to said template.

27. The process of claim 22, wherein said template is a double stranded template and is denatured to single stranded form, said dextran-bound primer is complementary in sequence to a region of one of the template strands and a second primer is provided which is complementary in sequence to a region of the other strand of the template, and the second primer is also extended so as to form a complementary sequence copy of said template other strand.

28. The process of claim 22, wherein said dextran is bound to a solid support.

29. The process of claim 22, wherein said extension of the primer is conducted in situ in a biological sample.

30. The process of claim 29, wherein said biological sample is a plant or animal tissue sample, microorganism culture, or microorganism culture medium.

* * * * *